United States Patent [19]

Withycombe et al.

[11] 4,108,876
[45] Aug. 22, 1978

[54] 5-METHYL-ALPHA[(METHYLTHIO)METHYL]-2-FURAN ACROLEIN

[75] Inventors: Donald Arthur Withycombe, Lincroft; Anne Hruza, Bricktown; Manfred Hugo Vock, Locust; Christopher Giacino, Califon; Braja Dulal Mookherjee, Holmdel; Alan Owen Pittet, Atlantic Highlands; William L. Schreiber, Jackson, all of N.J.

[73] Assignee: International Flavors & Fragrances Inc., New York, N.Y.

[21] Appl. No.: 827,211

[22] Filed: Aug. 24, 1977

Related U.S. Application Data

[62] Division of Ser. No. 753,462, Dec. 22, 1976, Pat. No. 4,064,279.

[51] Int. Cl.² .......................................... C07D 307/46
[52] U.S. Cl. ................................................. 260/347.2
[58] Field of Search ...................... 260/347.2; 426/535

[56] References Cited

U.S. PATENT DOCUMENTS 3,989,856  11/1976  Evers et al. ........................ 426/535

Primary Examiner—Richard L. Raymond
Attorney, Agent, or Firm—Arthur L. Liberman; Harold Haidt; Franklin D. Wolffe

[57] ABSTRACT

Processes and compositions are described for use in foodstuff flavors and as foodstuff article aroma and taste augmenting and enhancing materials of at least one alpha-substituted alkylidene methionals having the structure:

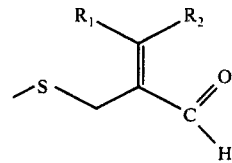

wherein $R_1$ or $R_2$ is one of the moieties:

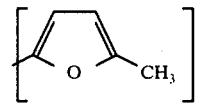

; or

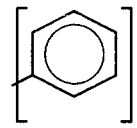

and the other is hydrogen or methyl. Addition of one or more alpha-substituted alkylidene methionals to foodstuff flavorings or to foostuffs is indicated to produce the following aroma and flavor characteristics, in the alternative taken together:

Aroma

Potato; Methional-like; Green; Hydrolyzed vegetable protein-like; Chicken-like; Cabbage; Green potato; Green weedy; Broccoli-like; and Green bean-like.

Flavor

Potato; Metallic; Sulfury-green; Cabbage-like; Chicken; Mushroom-like; Green-weedy; Broccoli-like; and Green bean-like. The compounds of our invention are useful in augmenting or enhancing the flavor and aroma nuances of vegetable (including potato and cabbage) and chicken flavors.

1 Claim, 10 Drawing Figures

EXAMPLE I

EXAMPLE I

EXAMPLE I

EXAMPLE I

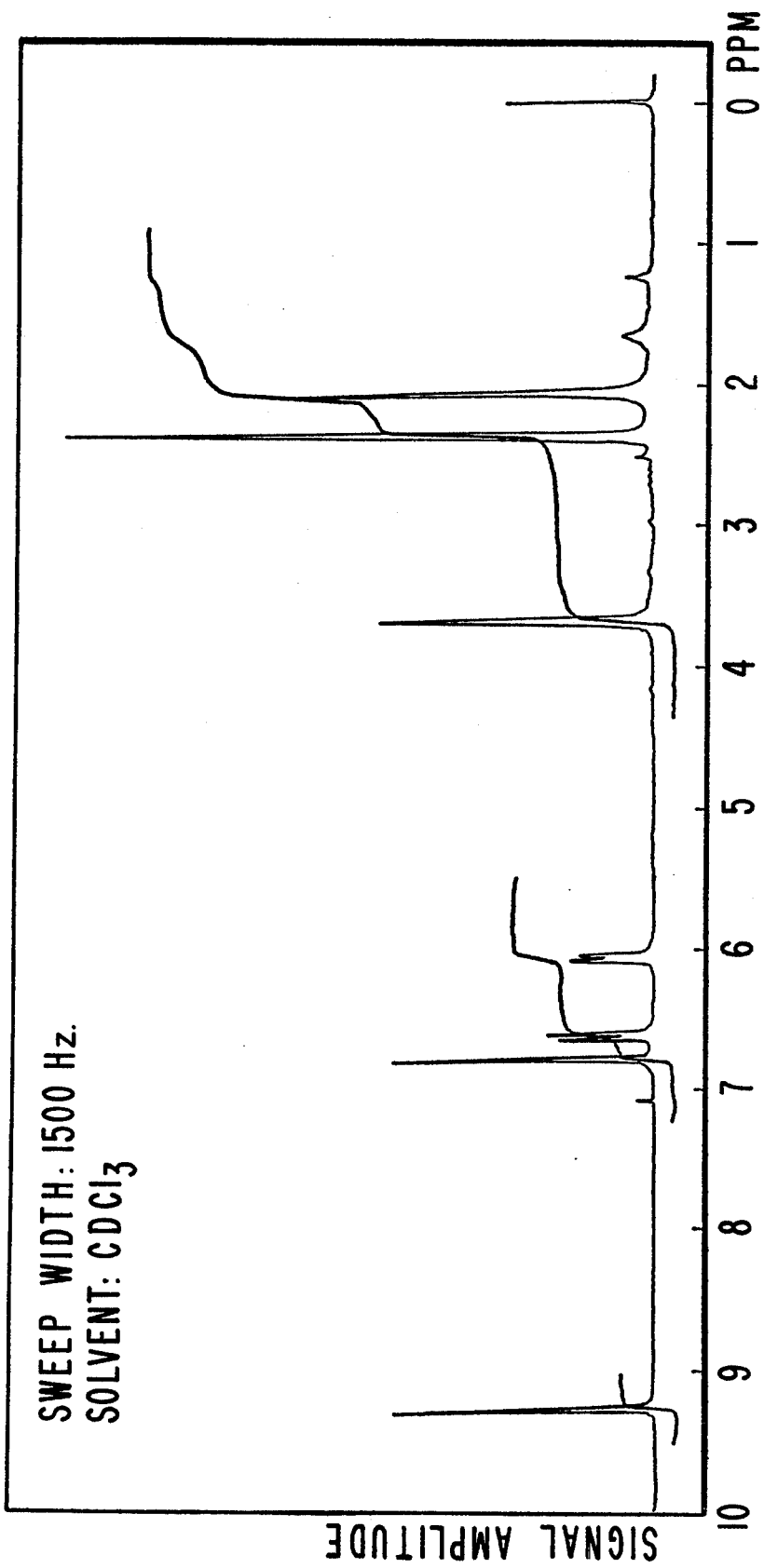

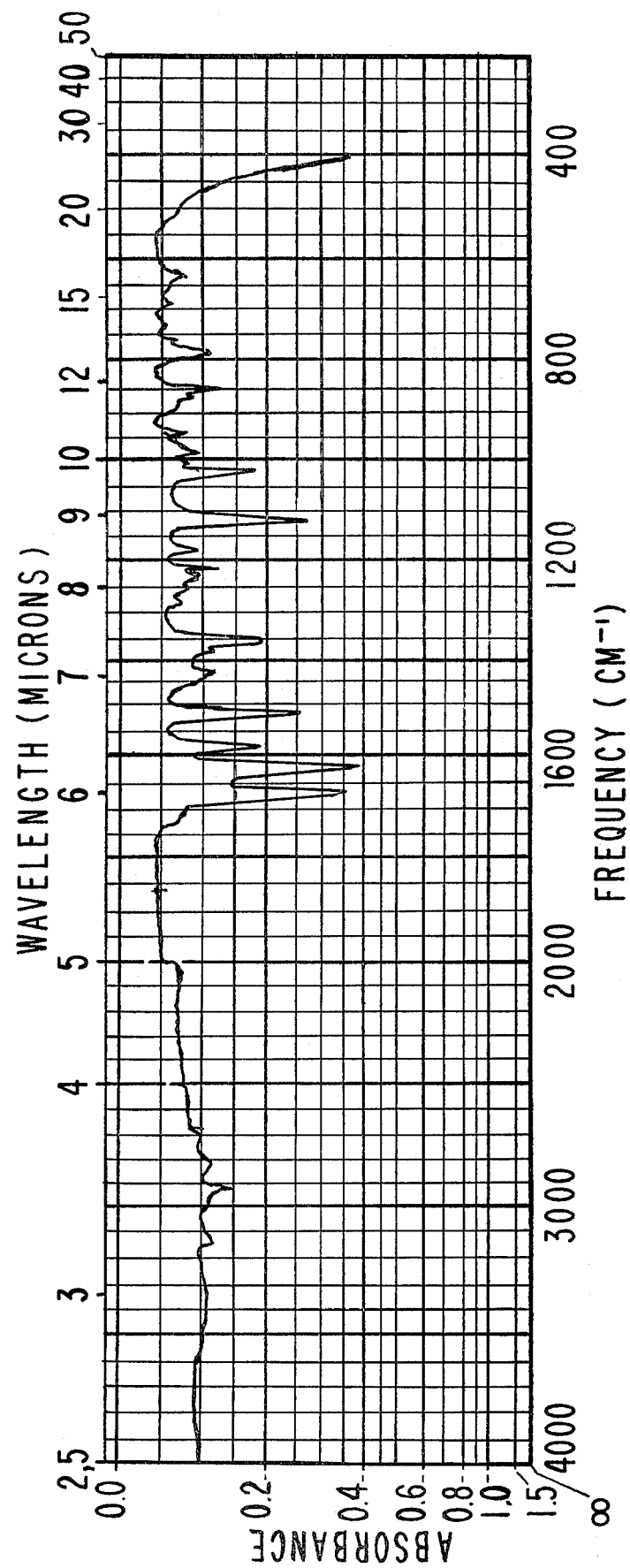

EXAMPLE II
MASS SPECTRAL PROFILE

EXAMPLE III
MASS SPECTRAL PROFILE

I R SPECTRUM FOR EXAMPLE IV

5-METHYL-ALPHA[(METHYLTHIO)METHYL]-2-FURAN ACROLEIN

This is a divisional of application Ser. No. 753,462, filed Dec. 22, 1976, now U.S. Pat. No. 4,064,279.

BACKGROUND OF THE INVENTION

The present invention relates to alpha-substituted alkylidene methionals and novel compositions using such compounds to augment or enhance the flavor and/or aroma of foodstuffs.

There has been considerable work performed relating to substances useful in augmenting or enhancing the flavor and/or aroma of variuos consumable materials including foodstuffs. These substances are used to supplement the use of natural materials, some of which may be in short supply and/or provide more uniform properties in the finished product. The following flavor and aroma notes are desirable, particularly in vegetable (including potato and cabbage) and chicken flavored foodstuffs:

Aroma

Potato; Methional-like; Green; Hydrolyzed vegetable protein-like; Chicken-like; Cabbage; Green potato; Green weedy; Broccoli-like; and Green bean-like.

Flavor

Potato; Metallic; Sulfury-green; Cabbage-like; Chicken; Mushroom-like; Green-weedy; Broccoli-like; and Green bean-like.

2,8-dithianon-4-ene-4-carboxaldehyde having the structure:

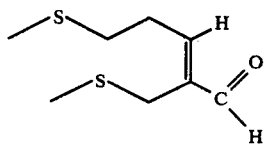

has been isolated from hydrolyzed vegetable protein distillate and has been found to have a sweet, meaty, hydrolyzed vegetable protein taste at 0.02 ppm, the threshold level. At 0.5 ppm 2,8-dithianon-4-ene-4-carboxaldehyde has a liver sausage, cabbage, potato, metallic, hydrolyzed vegetable protein-like, beef broth and methional aroma with liver sausage, cabbage, potato, hydrolyzed vegetable protein-like, beef broth-like, limburger cheese-like and methional-like flavor. The compound naturally-occurring in hydrolyzed vegetable protein distillate, has flavor and aroma nuances many of which are different in kind from the flavor and aroma nuances of the compounds of this invention.

Buttery, in an article entitled "Some Unusual Volatile Carbonyl Components of Potato Chips", J. Agr. Food Chem., Vol. 21, No. 1, 1973, pages 31–33, discloses compounds having the structures:

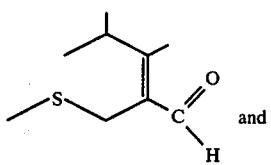

and

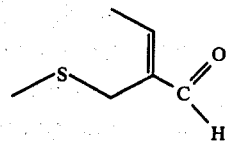

The compounds disclosed by Buttery are considered to have structures different in kind from the structures of the compounds of the instant invention. Furthermore, the flavor and aroma nuances of these compounds of Buttery are different in king from the flavor and aroma nuances of the compounds of the instant invention.

BRIEF DESCRIPTION OF THE DRAWINGS

FIG. 3 illustrates the NMR spectrum for the compound produced according to Example II.

FIG. 4 illustrates the Infrared spectrum for the compound produced according to Example II.

THE INVENTION

The present invention comprises novel compositions and foodstuffs containing alpha-substituted alkylidene methionals having the structure:

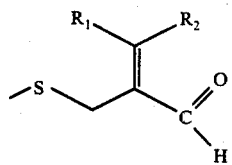

wherein $R_1$ or $R_2$ is one of the moieties:

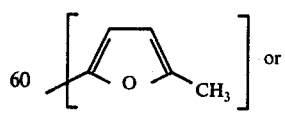 or 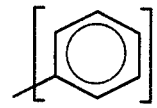

and the outer is hydrogen or methyl, the specific embodiments of which are described hereinafter by way of example and in accordance with which it is now preferred to practice the invention.

Such alpha-substituted alkylidene methionals are obtained by reacting an aldehyde or a methyl ketone with methional in the presence of a base according to the following reaction:

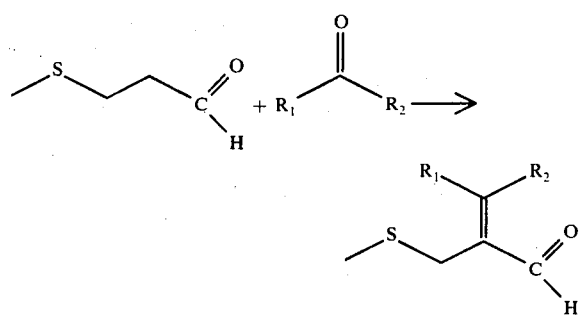

wherein $R_1$ and $R_2$ are as defined as above. This reaction takes place in the presence of a base such as alkali metal hydroxide or an alkali earth metal hydroxide. The reaction is well known as an "aldol condensation" type reaction. Examples of base which can be used in this reaction are lithium hydroxide, sodium hydroxide, potassium hydroxide and barium hydroxide. The concentration of base may vary between 0.1 molar up to 5 molar with a preferred concentration range of from 0.3 molar up to 0.8 molar. The reaction temperature range is between −10° and 50° C with a temperature of reaction being a function of the particular base catalyst used.

The mole ratio of methional to methyl ketone or aldehyde is not critical, but most convenient is a mole ratio of 1:1.

At the end of this invention the reaction mass is "worked by" by extracting the reaction product with a solvent such as methylene chloride and then treating the organic layer with weak acid and weak base and finally fractionally distilling the resulting reaction product, e.g., by means of vacuum distillation.

Specific examples of alpha-substituted alkylidene methionals produced using the afore-mentioned process and their food flavor properties are as follows (as set forth in Table I below):

Table I

| Compound | Structure | Flavor Property |
|---|---|---|
| 2-[(methylthio)methyl]-3-phenyl-2-propenal | 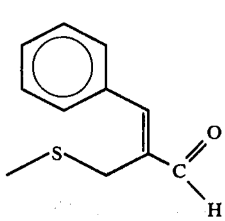 | A green weedy, broccoli-like, green bean-like aroma with a green weedy, broccoli-like and green bean-like flavor at 20 ppm. |

Table I-continued

| Compound | Structure | Flavor Property |
|---|---|---|
| 5-methyl-alpha[(methylthio)methyl]-2-furan acrolein | 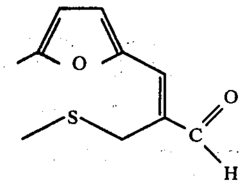 | A potato-like, methional-like, green sulfury, hydrolyzed vegetable protein, chicken-like, cabbage, green potato-like aroma character with potato-like, metallic sulfury green, cabbage-like, chicken and mushroom-like flavor nuances at 1ppm. |

Figure 1A:
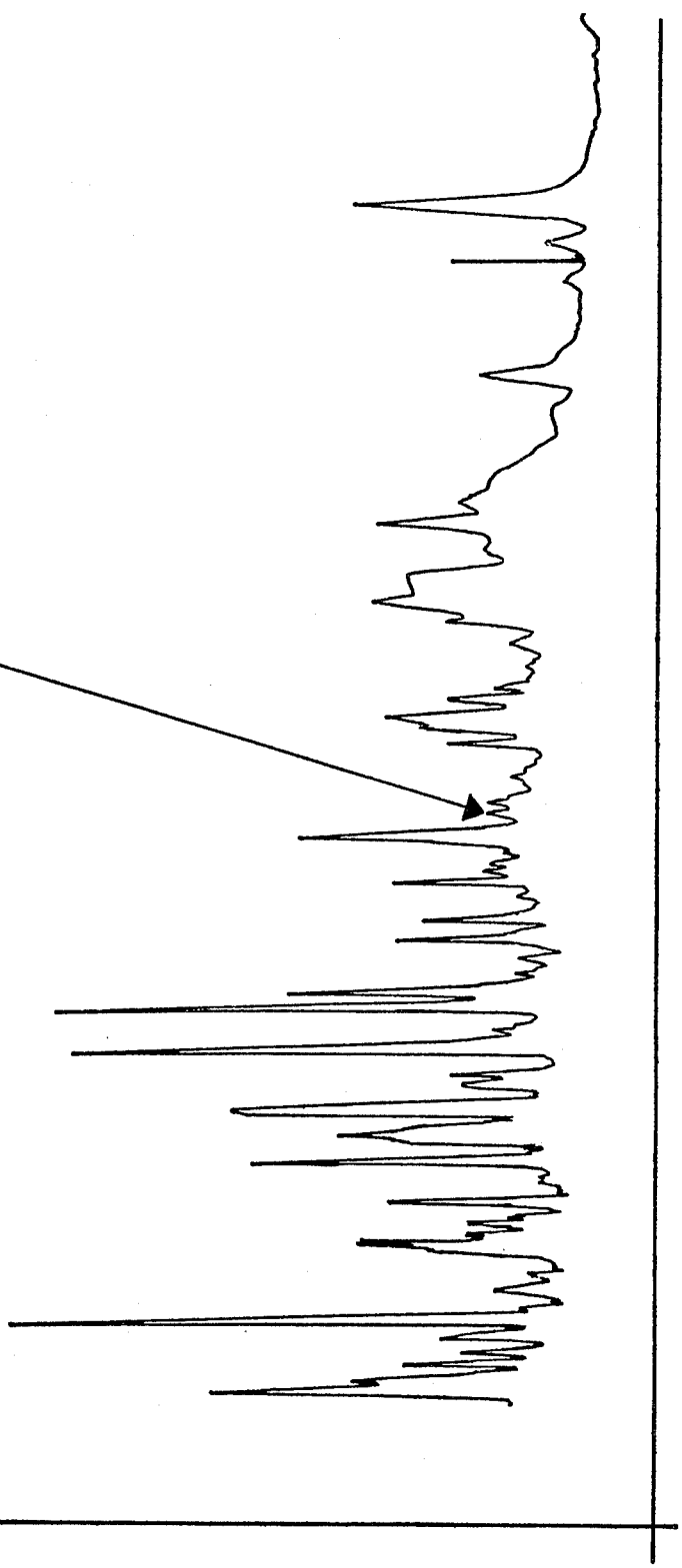
FIG. 1A illustrates the GLC spectrum for 2-[(methylthio)methyl]-3-phenyl-2-propenal produced according to Example I.
Figure 1B:
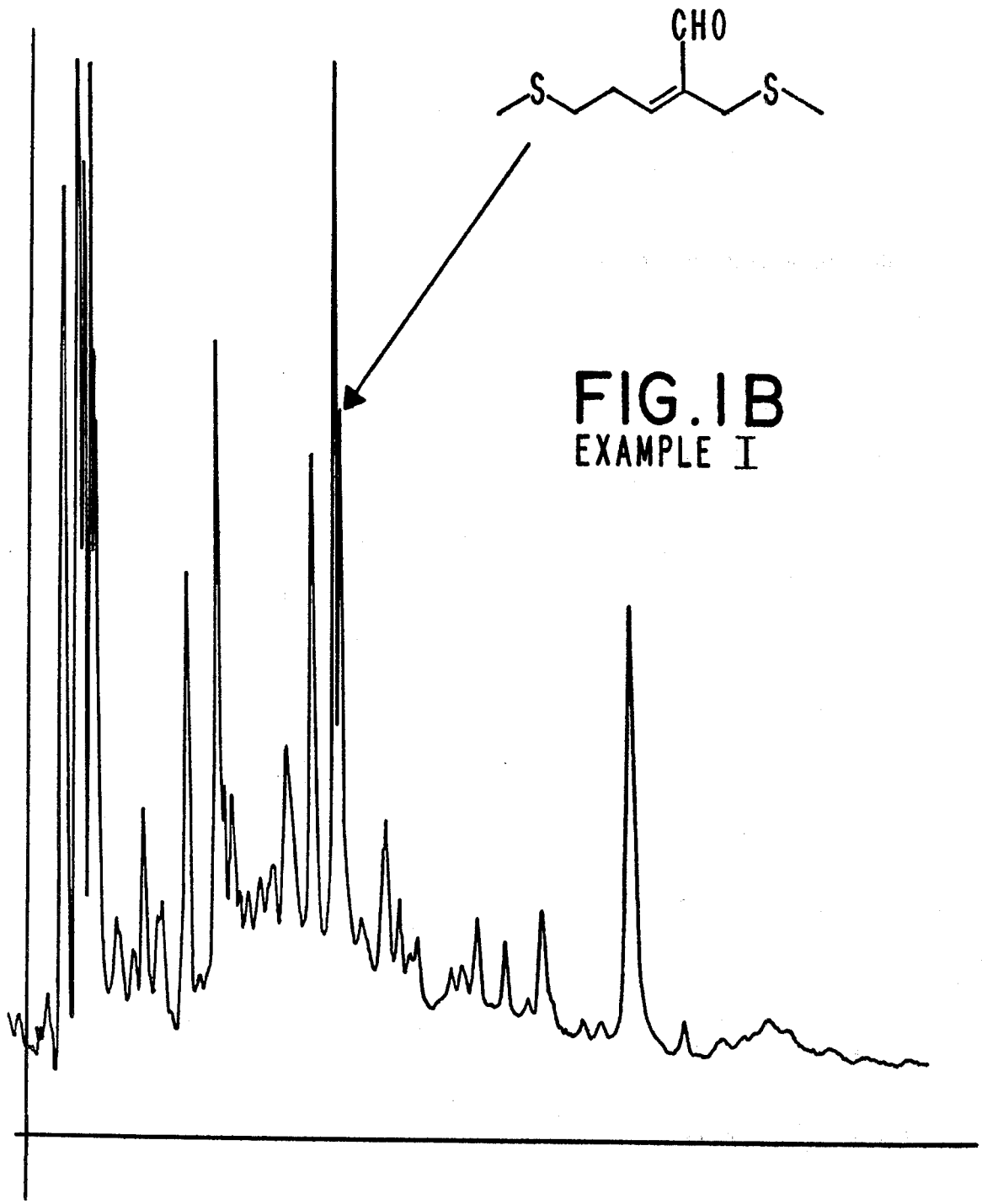
FIG. 1B illustrates the GLC spectrum for the neutral fraction containing 2,8-dithianon-4-ene-4-carboxaldehyde.

The distillate of hydrolyzed vegetable protein (as produced according to Example I, infra), appears to contain the following alpha-substituted alkylidene methionals:
2-[(methylthio)methyl]-3-phenyl-2-propenal; and
2,8-dithianon-4-ene-4-carboxaldehyde. The presence of the foregoing materials in the distillate of hydrolyzed vegetable protein is indicated in various peaks in FIGS. 1A and 1B, respectively. The presence of such compounds in hydrolyzed vegetable protein distillate is not considered to infer that these compounds can be used as foodstuff flavorants or that they can be used in order to augment or enhance the flavor or aroma of a foodstuff.

When the alpha-substituted alkylidene methionals of our invention are used as food flavor adjuvants, or are used to augment or enhance the flavor or aroma characteristics of foodstuffs, the nature of the co-ingredients included with the said alpha-substituted alkylidene methionals in formulating the product composition will also serve to augment the organoleptic characteristics of the ultimate foodstuff treated therewith.

As used herein in regard to flavors, the term "augment" in its various forms means "supplying or imparting flavor character or note to otherwise bland, relatively tasteless substances or augmenting the existing flavor characteristic where a natural flavor is deficient in some regard or supplementing the existing flavor impression to modify its quality, charactor or taste."

As used herein in regard to food flavors, the term "enhance" is used herein to mean the intensification of a flavor or aroma characteristic or note without the modification of the quality thereof. Thus, "enhancement" of a flavor or aroma means that the enhancement agent does not add any additional flavor note.

As used herein the term "foodstuff" includes both solids and liquids, and ingestible materials or chewable but non-ingestible materials such as chewing gum. Such materials usually do, but need not, have nutritional value. Thus, foodstuffs include soups, convenience foods, beverages, gelatin desserts, dairy products, candies, vegetables, cereals, soft drinks, snacks and the like.

Substances suitable for use herein as co-ingredients or flavoring adjuvants are well known in the art for such use, being extensively described in the relevant literature. Apart from the requirements that any such materials be organoleptically compatible with the alpha-substituted alkylidene methionals, non-reactive with the alpha-substituted alkylidene methionals of our invention and "ingestibly" acceptable and thus non-toxic or otherwise non-deleterious, nothing particularly critical resides in the selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include vanillin, ethyl vanillin, diacetyl, phenethyl 2-furoate, maltol, neryl butyrate, amyl butyrate, allyl caproate, citral, 4-methylthiobutanal, 2-trans hexenal, dimethyl sulfide, linalool, acetic acid, methyl sulfide, acetaldehyde, isovaleraldehyde, isoamyl alcohol, acetic acid, lactones, including δ-decalactone, δ-undecalactone and γ-nonalactone, isoamyl esters including the acetate, butyrate and octanoate, pyrazines such as dimethyl pyrazine, 2-ethyl-3-methyl pyrazine, 2-ethyl-3-methyl pyrazine, 2,3-diethyl-5-methyl pyrazine, 2-ethyl-3-acetyl pyrazine, tetramethyl pyrazine, 2-methyl pyrazine, amyl octanoate, benzoic acid, pyridine, phenylacetic acid, cinnamyl esters such as the propionate, 4-phenyl-3-butene-2-one, 3-phenyl-2-pentenal, 3-phenyl-3-pentenal, 3-phenyl-4-pentenal, 2-phenyl-2-methyl-4-pentenal, 2-phenyl-4-pentenal, 2-phenyl-4-pentenal dimethyl acetal, 2-isobutylthiazole, 2-(secondary butyl) thiazole, 2-(i-propyl) thiazole and 2-(n-propyl) thiazole. These are combined in proportions requisite to obtain the desired effect as illustrated further hereinbelow.

As will be appreciated by those skilled in the art, the amount of alpha-substituted alkylidene methionals employed in a particular instance can vary over a relatively wide range whereby to its desired organoleptic effects having reference to the nature of the product are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter the organoleptic characteristics of the parent composition.

The use of insufficient quantities of alpha-substituted alkylidene methionals will, of course, substantially vitate any possibility of obtaining the desired results while excess quantities prove needlessly costly and in extreme cases may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of alpha-substituted alkylidene methionals ranging from a small but effective amount, e.g., abut 0.02 parts per million up to about 50 parts per million by weight based on total composition (more preferably from about 0.2 ppm up to about 25 ppm) are suitable. Concentrations in excess of the maximum quantity stated are not normally recommended, since they fail to prove commensurate enhancement of organoleptic properties. In those instances, wherein the alpha-substituted alkylidene methionals is added to the foodstuff as an integral component of a flavoring composition, it is, of course, essential that the total quantity of flavoring composition employed be sufficient to yield an effective alpha-substituted alkylidene methional concentration in the foodstuff product.

Food flavoring compositions prepared in accordance with the present invention preferably contain the alpha-substituted alkylidene methional in concentrations ranging from about 0.1% up to about 15% by weight based on the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the alpha-substituted alkylidene methionals with, for example, gum arabic, gum tragacanth, carrageenan and the like, and thereafter spraydrying the resultant mixture whereby to obtain the particular solid product. Pre-prepared flavor mixes in powder form, e.g., a fruit-flavored powder mix, are obtained by mixing the dried solid components, e.g., starch, sugar and the like and alpha-substituted alkylidene methionals in a dry blender until the requisite degree of uniformity is achieved.

It is presently preferred to combine with the alpha-substituted alkylidene methionals, the following adjuvants:

Acetaldehyde;
Isobutyraldehyde;
Isovaleraldehyde;
Methyl sulfide;
Methyl disulfide;
Isobutyl acetate;

Phenylethyl acetate;
Diacetyl;
Acetophenone;
Furfural (50%);
Benzaldehyde;
Phenylacetaldehyde;
Isoamyl alcohol;
Phenylethyl alcohol;
Gamma-butyrolactone;
3-Phenyl-4-pentenal;
3-Phenyl-3-pentenal;
3-Phenyl-2-pentenal;
Methyl pyrazine;
Tetramethyl pyrazine;
Trimethylpyrazine;
2,6-Dimethylpyrazine;
2-Ethyl-3-methylpyrazine;
2-Ethyl-3,5-dimethylpyrazine;
2-Ethyl-3,6-dimethylpyrazine;
2-Ethyl-5-methylpyrazine;
2-Ethyl-3-acetyl pyrazine;
2-(i-butyl) thiazole;
2-(i-propyl) thiazole;
2-(n-propyl) thiazole;
2-Phenyl-4-pentenal;
2-Phenyl-4-pentenaldimethylacetal;
4-Methylthiobutanal;
trans-2-hexenal;
Hydrolyzed vegetable protein;
Monosodium glutamate;
Black pepper oil;
Nutmeg oil;
Celery oil;
Lemon oil;
Mustard oil.

The following examples are given to illustrate embodiments of the invention as it is presently preferred to practice it. It will be understood that these examples are illustrative and that the invention is not to be considered as restricted thereto except as indicated in the appended claims.

EXAMPLE I

Figure 2A:
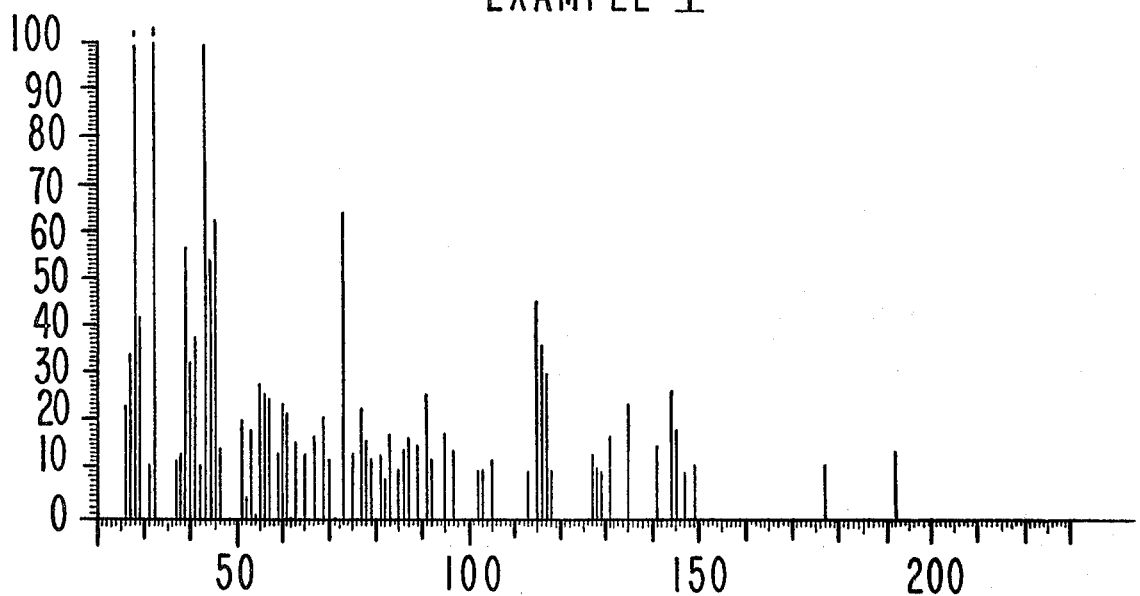
FIG. 2A illustrates the Mass Sprectrum for 2-[(methylthio)methyl]-3-phenyl-2-propenal produced according to Example I.
Figure 2B:
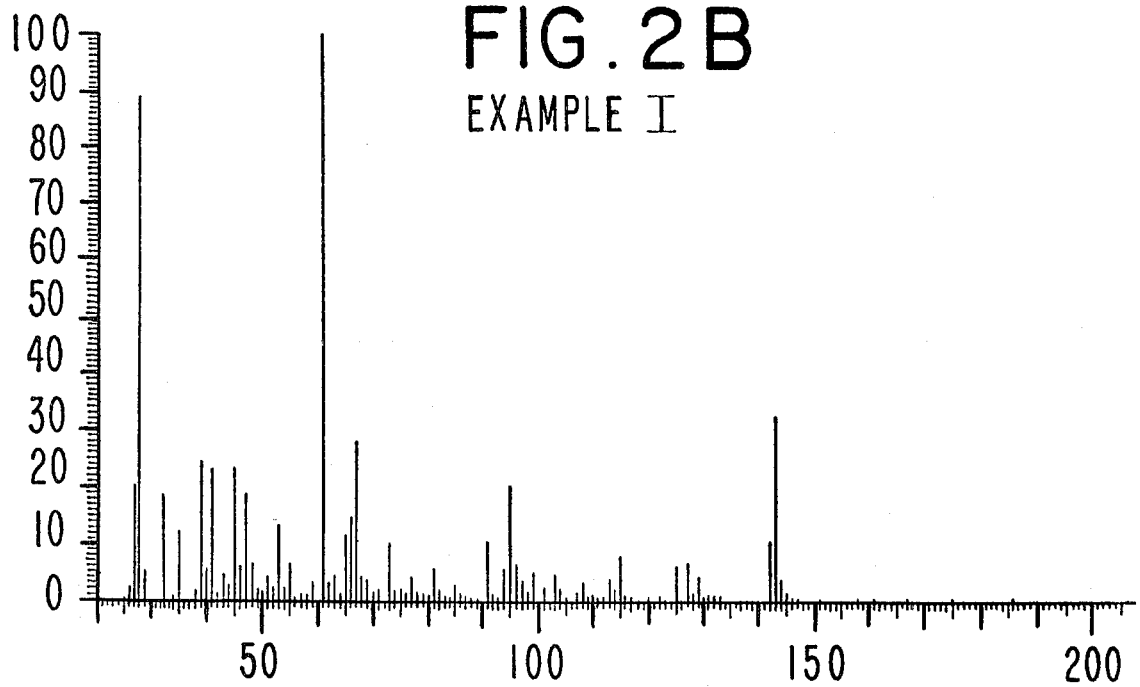
FIG. 2B illustrates the Mass Spectrum for the neutral fraction containing 2,8-dithianon-4-ene-4-carboxaldehyde.

PREPARATION AND ANALYSIS OF DISTILLATE OF HYDROLYZED VEGETABLE PROTEIN 240 pounds of Nestle 4-BE hydrolyzed vegetable protein is intimately admixed with 240 pounds deionized water. The resulting mixture is metered into a Turbofilm evaporator and distilled under atmospheric pressure whereby 20% is recovered as an aqueous distillate and 80% is discarded. The aqueous distillate is then subjected to extraction in a 22 liter round bottom liquid-liquid extractor. The extractor is charged with the aqueous distillate and saturated with sodium chloride. The resulting mixture is extracted with diethyl ether. The ether extract is then evaporated using a 5 liter Kuederna-Danish evaporator. The resulting material is then fractionated into acidic, phenolic, basic and neutral components. Each of the fractions is analyzed using GLC, NMR, IR and mass spectral analyses. Evidence is obtained by the foregoing analyses which indicate that the following alpha-substituted alkylidene methionals may be present in the neutral fraction:
2,8-dithianon-4-ene-4-carboxaldehyde; and
2-[(methylthio)methyl]-3-phenyl-2-propenal. The GLC spectrum for the neutral fraction containing 2,8-dithianon-4-ene-4-carboxaldehyde is set forth in FIG. 1B and the MS analysis is set forth in FIG. 2B. Evidence for 2-[(methylthio)methyl]-3-phenyl-2-propenal is set forth in the GLC spectrum of the neutral fraction in FIG. 1A and the MS analysis of the compounds is set forth in FIG. 2A.

EXAMPLE II

PREPARATION OF 5-METHYL-ALPHA-[(METHYLTHIO)METHYL]-2-FURAN ACROLEIN

Reaction:

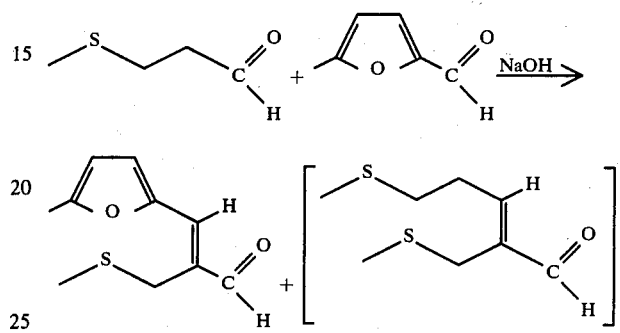

Into a 1 liter reaction flask equipped with mechanical stirrer, 250 ml addition funnel, Y adaptor, thermometer and Friedrich condenser is placed 104 grams methional and 110 grams of 5-methyl furfural. The reaction mass is cooled to 0° C and 100 ml of a 0.5 molar solution of sodium hydroxide is added dropwise with stirring. The reaction mass is permitted to stir at 0° C for 2 hours. The resulting reaction mass is extracted with three 100 ml portions of methylene chloride and the extracts are combined, dried over anhydrous sodium sulfate and evaporated on a rotary evaporator. The resulting product is distilled on a short path column, boiling point 155° C (5 mm Hg).

The NMR data are as follows:

| Chemical Shift (ppm) | Assignment | Integration |
|---|---|---|
| 2.06 (s) | $CH_3-S-$ | 3H |
| 2.36 (s) | $CH_3-\overset{\overset{O}{\|\|}}{C}-O-$ | 3H |
| 3.68 (S) | $C=C-CH_2-S-$ | 2H |
| 6.06 (d, J=4H$_z$) | Furan protons | 1H |
| 6.62 (d, J=4H$_z$) | | 1H |
| 6.78 (s) | Olefinic proton | 1H |
| 9.26 (s) | HC=O | 1H |

The Infrared data are as follows:
Absorption Bands cm$^{-1}$ 780, 850, 1015, 1120, 1210, 1355, 1420, 1500, 1570, 1615, 1665, 2910.

The Mass Spectral data are as follows:

| m/e | Relative Intensity (%) |
|---|---|
| 43 | 53 |
| 51 | 14 |
| 65 | 12 |
| 77 | 42 |
| 91 | 34 |
| 93 | 23 |
| 105 | 11 |
| 119 | 14 |
| 120 | 22 |
| 121 | 19 |
| 149 | 100 |
| 150 | 11 |

| m/e | Relative Intensity (%) |
| --- | --- |
| 196 | 62 |

Figure 5:
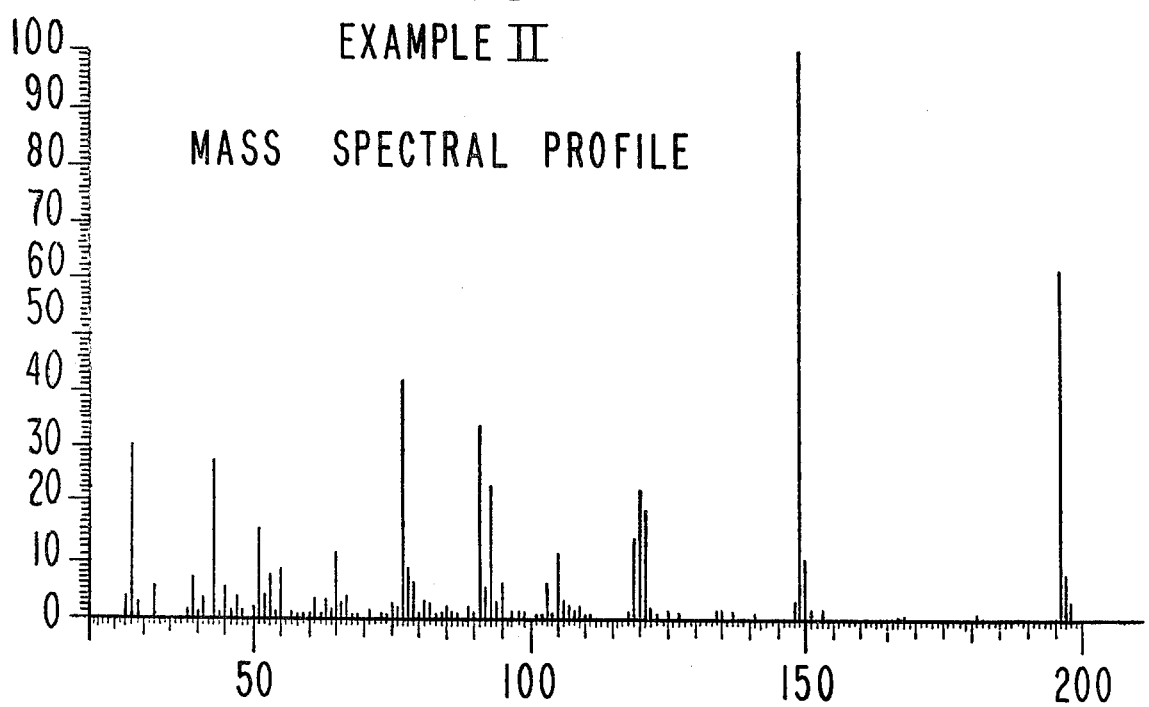
FIG. 5 illustrates the Mass Spectrum for the compound produced according to Example II.

The NMR spectrum is set forth in FIG. 3. The Infrared spectrum is set forth in FIG. 4. The Mass Spectrum is set forth in FIG. 5.

EXAMPLE III

PREPARATION OF 2,8-DITHIANON-4-ENE-4-CARBOXALDEHYDE

Reaction:

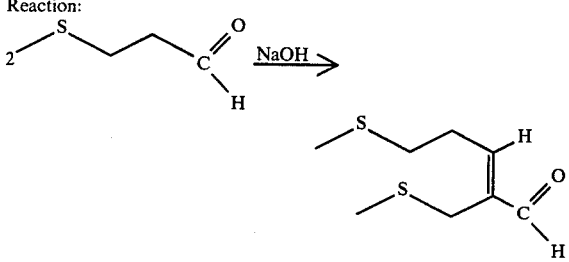

Into a 1 liter reaction flask equipped with mechanical stirrer, 250 ml addition funnel, Y adapter, thermometer and Friedrich condenser is placed 208 grams of methional. The reaction mass is cooled to 0° C and 100 ml of a 0.5 molar solution of sodium hydroxide is added dropwise with stirring. The resulting reaction mass is extracted with three 100 ml portions of methylene chloride and the extracts are combined, dried over anhydrous sodium sulfate and evaporated on a rotary evaporator. The resulting product was then subjected to vacuum distillation to give the product, boiling point 129° C (1 mm Hg).

Figure 6:
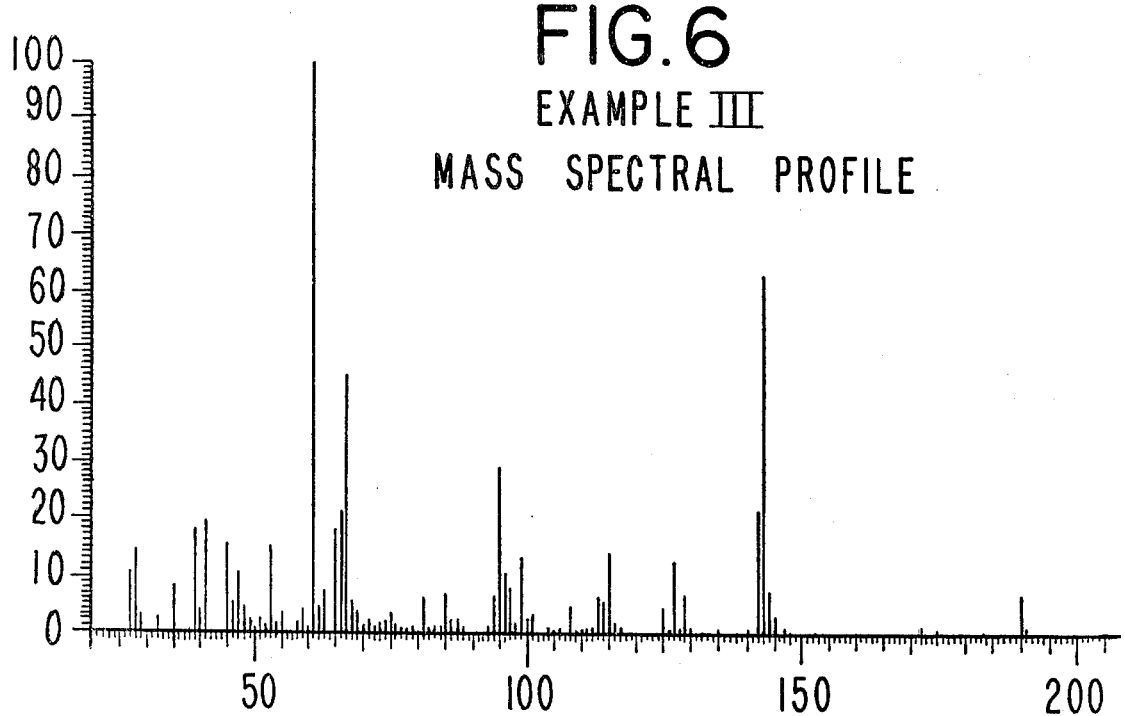
FIG. 6 illustrates the Mass Spectrum for the compound produced according to Example III.

The Mass Spectrum is set forth in FIG. 6.

EXAMPLE IV

PREPARATION OF 2-[(METHYLTHIO)METHYL]-3-PHENYL-2-PROPENAL

Reaction:

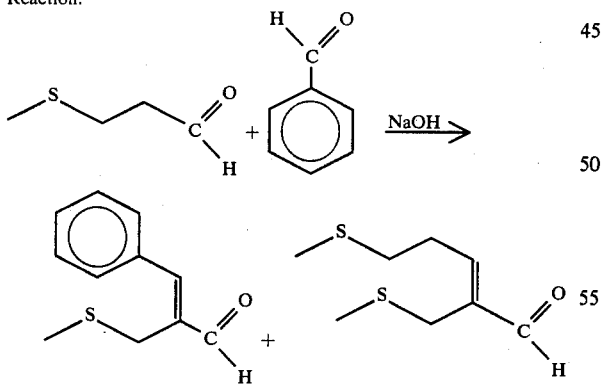

Into a 100 ml three necked reaction flask equipped with stirrer, thermometer and addition funnel is charged a solution of 0.5 grams of potassium hydroxide in 10 ml methanol. Benzaldehyde (10.0 grams) is added as the mixture is cooled to 5°–10° C. Methional (10.0 grams) is then added dropwise while maintaining the reaction temperature at 5°–10° C. The mixture is then allowed to warm to room temperature and stirred for a period of 1 hour. Most of the solvent is evaporated at reduced pressure and the mixture is partitioned between water and ether. The organic layer is washed several times with water and once with saturated brine. The solvent is evaporated leaving a yellow oil wich is distilled to give 6.1 grams product, boiling point 104°–111° C (0.4 mm Hg).

The distillate is crystallized from ether-hexane and then recrystallized twice from ether to give 1.5 grams of colorless needles, melting point 30.4°–31.0° C.

The NMR data is as follows:

| Chemical Shift (ppm) | Assignment | Integration |
| --- | --- | --- |
| 2.12 (s) | $CH_3S$ | 3H |
| 3.56 (s) | $=C-CH_2-S-$ | 2H |
| 7.62–7.19 (m) | aromatic protons + olefinic protons | 6H |
| 9.53 (s) | $HC=O$ | 1H |

The Infrared absorption bands are as follows:
$cm^{-1}$ 695, 740, 755, 865, 1125, 1200, 1320, 1430, 1450, 1620, 1680, 2920.

The Mass Spectral data is as follows:

| m/e | Relative Intensity (%) |
| --- | --- |
| 29 | 22 |
| 39 | 24 |
| 45 | 22 |
| 63 | 18 |
| 91 | 28 |
| 115 | 100 |
| 116 | 93 |
| 117 | 56 |
| 144 | 44 |
| m 192 | 18 |

Figure 7:
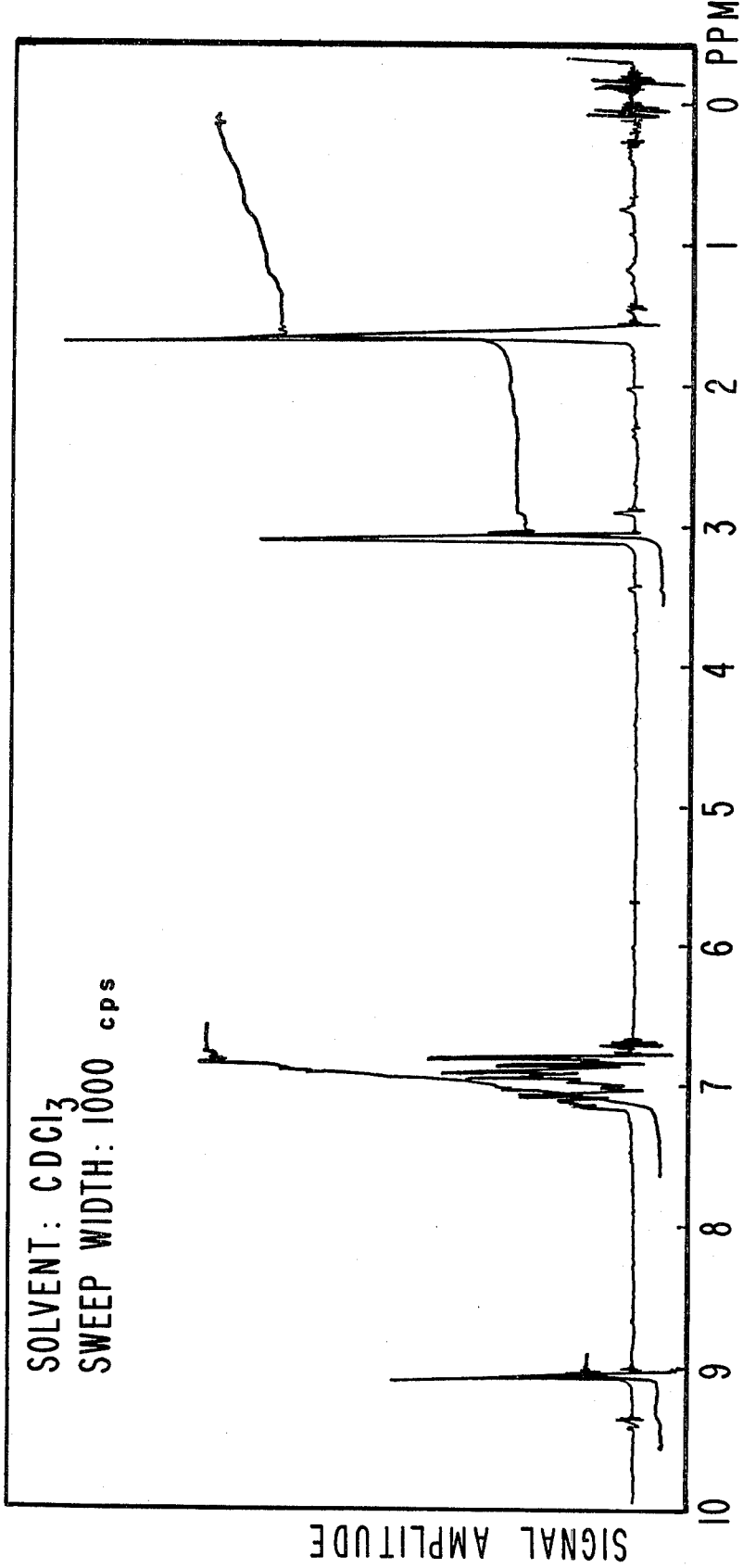
FIG. 7 illustrates the NMR spectrum for the compound produced according to Example IV.
Figure 8:
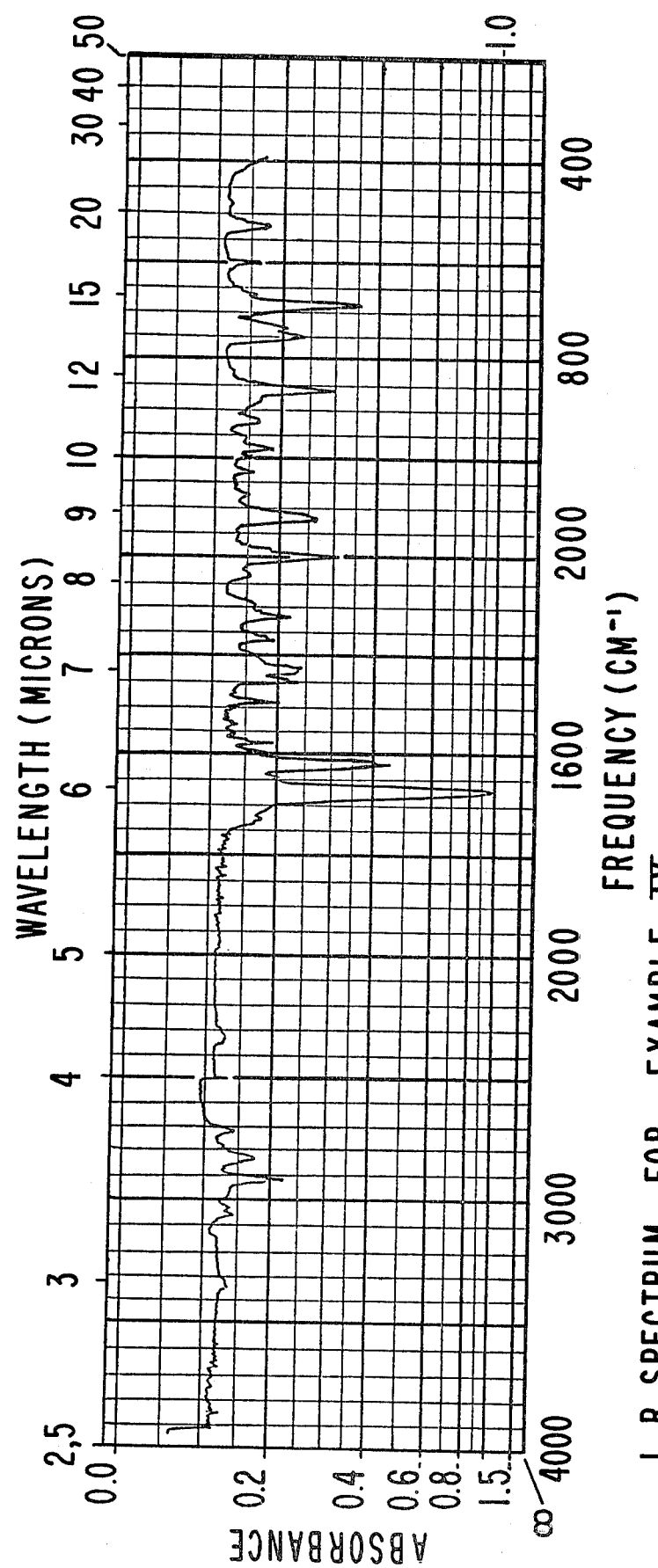
FIG. 8 illustrates the Infrared spectrum for the compound produced according to Example IV.

The NMR spectrum is set forth in FIG. 7. The Infrared spectrum is set forth in FIG. 8.

EXAMPLE V

To a portion of a standard salad dressing, 2-[(methylthio)methyl]-3-phenyl-2-propenal prepared according to Example IV is added at a rate of 0.10 ppm. The resulting mixture has a characteristic broccoli/green fava bean note. The salad dressing is a mixture of the following:

| Ingredient | Parts |
| --- | --- |
| Black pepper oil | 3 |
| Nutmeg oil | 3 |
| Celery oil | 3 |
| Lemon oil | 3 |
| Mustard oil | 1 |
| Vinegar-citric acid (50:50 mixture) | 120 |
| Starch paste prepared from tapioca flour-water (50:50 mixture) | 300 |
| Liquid egg yolks | 210 |
| Sodium chloride | 7 |
| Sucrose | 10 |
| Mustard | 20 |
| Locust Bean gum | 6 |

EXAMPLE VI

POTATO FLAVOR

A potato flavoring material is prepared by admixing the following ingredients:

| Ingredient | Parts by Weight |
| --- | --- |
| Diacetyl (1% solution) | 0.20 |
| Furfural | 0.2 |
| 2-acetyl-3-ethyl pyrazine (1% solution) | 1.0 |

-continued

| Ingredient | Parts by Weight |
| --- | --- |
| 2-ethyl-3-methyl pyrazine | 4.0 |
| methional | 2.0 |
| 5-methyl-alpha-[(methylthio) methyl]-2-furan acrolein (prepared according to Example II) | 0.2 |
| ethanol (95% food grade) | 91.6 |

A bench panel of five individuals compared the above formulation with one not containing any 5-methyl-alpha-[(methylthio)methyl]-2-furan acrolein but identical in all other respects. The formulations were compared at the rate of 10 ppm in water solutions. It was concluded that the 5-methylalpha-[(methylthio)methyl]-2-furan acrolein imparted to the flavor a mashed potato-like taste with cabbage nuances.

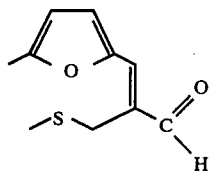

What is claimed is:

1. 5-Methyl-alpha[(methylthio)methyl]-2-furan acrolein having the structure: